United States Patent [19]

DeBernardis et al.

[11] 4,440,769

[45] Apr. 3, 1984

[54] 2-(4-PHENYLALKANOYLPIPERAZIN-1-YL) QUINAZOLINE COMPOUNDS, PHARMACEUTICAL COMPOSITIONS AND METHOD OF PRODUCING $\alpha_1$ ANTAGONISTIC ACTIVITY

[75] Inventors: John F. DeBernardis, Lake Villa; Martin Winn, Deerfield, both of Ill.

[73] Assignee: Abbott Laboratories, North Chicago, Ill.

[21] Appl. No.: 465,846

[22] Filed: Feb. 11, 1983

[51] Int. Cl.³ .................. A61K 31/505; C07D 403/04
[52] U.S. Cl. .................................... 424/251; 544/291
[58] Field of Search ....................... 544/291; 424/251

[56] References Cited

U.S. PATENT DOCUMENTS

| | | | |
|---|---|---|---|
| 3,511,836 | 5/1970 | Hess | 260/256.4 |
| 3,635,979 | 1/1972 | Hess | 260/256.4 |
| 3,663,706 | 5/1972 | Hess | 424/251 |
| 4,092,315 | 5/1978 | Bianco | 544/291 |

OTHER PUBLICATIONS

The Journal of Biological Chemistry, vol. 257, No. 24, Issue of 12/25, pp. 15174–15181, 1982.
Proc. Natl. Acad. Sci., U.S.A., vol. 79, pp. 2186–2190, Apr. 1982, Biochemistry.
The Journal of Biological Chemistry, vol. 257, No. 20, Issue of Oct. 25, pp. 12332–12340, 12341–12350, 1982, U.S.A.
Federation Proceedings, Mar. 10, 1982, vol. 41, No. 5, Abstract 7064.

*Primary Examiner*—Mary C. Lee
*Assistant Examiner*—James H. Turnipseed
*Attorney, Agent, or Firm*—Dennis K. Shelton; Martin L. Katz

[57] ABSTRACT

4-amino-6,7-dimethoxy-2-(4-phenylalkanoylpiperazin-1-yl) quinazolines having $\alpha_1$-adrenergic receptor antagonistic activity. These compounds are useful in the treatment of hypertension.

16 Claims, No Drawings

2-(4-PHENYLALKANOYLPIPERAZIN-1-YL) QUINAZOLINE COMPOUNDS, PHARMACEUTICAL COMPOSITIONS AND METHOD OF PRODUCING $\alpha_1$ ANTAGONISTIC ACTIVITY

BACKGROUND OF THE INVENTION

This invention relates to certain 2-(4-phenylalkanoylpiperazin-1-yl) quinazoline compounds, pharmaceutical compositions and methods of producing $\alpha_1$-antagonistic activity. More particularly, this invention relates to certain 4-amino-6,7-dimethoxy-2-(4-phenyl-alkanoylpiperazin-1-yl) quinazoline compounds which exhibit a high degree of selective affinity for $\alpha_1$-adrenergic receptor binding sites.

The adrenergic nervous system plays a primary role in the neurogenic regulation of the cardiovascular system. The sympathetic outflow to the heart and peripheral vessels originates from the vasomotor center and travels along descending neuronal pathways interrupted by synapses, the switching units which transmit the neurological signal from higher to lower neurons and from nerve endings to cells of the effector organ. Transmission of the neurological signal across synapses is mediated chemically by a neurotransmitter which is stored in the vesicles of nerve endings. Upon arrival of the neurological signal, regulated quantities of neurotransmitter are released into the synapse where it combines with receptor sites in the cellular membrane of the next neuron or effector organ, and excites the receptor cell to propagate the neurological signal or to produce an effect in an effector organ.

The principal natural neurotransmitters specific to the adrenergic nervous system are norepinephrine and epinephrine (hereinafter "norepinephrine"), which mediate neurological transmission in some central noradrenergic neurons in the vasomotor center and elsewhere in the brain as well as peripherally in so-called postganglionic sympathetic neurons. Receptors for norepinephrine have been recognized to be proteins bound to membranes of effector cells. These receptors control the function of the effector cell, and through it the function of a whole organ or organ systems. Norepinephrine receptors are highly specific for norepinephrine and can discriminate between it and many other transmitters and molecules. However, their discrimination capability is not complete, and other related catecholamines as well as various synthetic agents have been found to bind to norepinephrine receptors.

Through observed responses of various tissues and organs to norepinephrine and related catecholamine-like compounds, it has been found that norepinephrine receptors differ substantially in different tissues where they mediate different functions. In addition, norepinephrine receptors from various tissues have been found to differ in their discriminatory abilities for other compounds. Based on the foregoing and other observations, norepinephrins receptors have been classified into at least two major groups, i.e., the $\alpha$-adrenergic receptors and the $\beta$-adrenergic receptors. In addition, the $\alpha$-groups of receptors have been further divided into the $\alpha_1$-adrenergic receptor sub-group and the $\alpha_2$-adrenergic receptor sub-group. The $\alpha_1$-adrenergic receptors have been characterized as being exitatory in nature, primarily functioning to result in peripheral vascular contraction. On the other hand, the $\alpha_2$-adrenergic receptors have been characterized as being inhibitory in nature, primarly functioning to inhibit transmitter release through inhibition of adenylate cyclase activity.

Inasmuch as the different groups and sub-groups of adrenergic receptors mediate different functions in different bodily tissues and organs, it is highly desirable to obtain chemical compounds or entities which are highly selective for limited types of receptor sites. In this manner, isolated symptoms can be effectively treated, without affecting other unrelated tissues and organs, by selectively agonizing or antagonizing a particular sub-group of receptor sites.

One compound which has been found to selectively antagonize $\alpha_1$-adrenergic receptor sites is known generically as prazosin. The structure of prazosin is as follows:

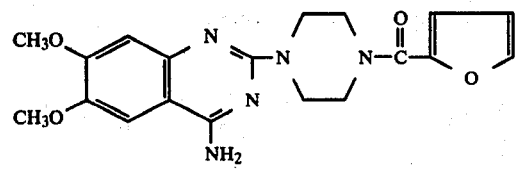

Due to its $\alpha_1$-adrenergic receptor selectivity and its antagonistic activity, prazosin is used as an antihypertensive agent to block $\alpha_1$-mediated vascular contraction. Prazosin has also been used as a model $\alpha_1$-antagonist in the evaluation of other compounds for $\alpha_1$-agonistic or -antagonistic activity and in the characterization of $\alpha_1$-receptor sites. The compound prazosin is disclosed in U.S. Pat. Nos. 3,511,836; 3,635,979; 3,663,706; and 4,092,315.

Although prazosin has been found to be useful as an $\alpha_1$-adrenergic receptor antagonist, the search continues for new compounds having improved properties. One such compound, 2-(4-[4-azido-benzoyl]-piperazin-1-yl)-4-amino-6,7-dimethoxyquinazoline having the structure:

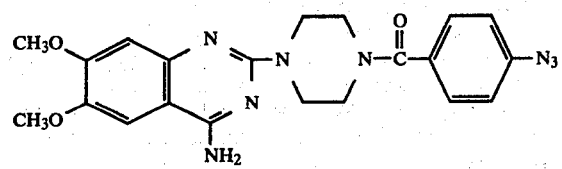

has been disclosed in *Federation Proceedings*, Vol. 41, No. 5, Abst. No. 7064, p. 1478 (Mar. 10, 1982), as exhibiting irreversible non-competitive $\alpha_1$-adrenergic receptor inhibition upon photolysis.

SUMMARY OF THE INVENTION

It has now been found that compounds of the formula

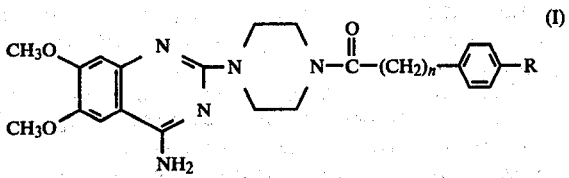

wherein n is 3, 4 or 5, and R is —NH$_2$, or —N$_3$, or a pharmaceutically acceptable salt thereof exhibit highly selective $\alpha_1$-adrenergic receptor antagonistic activity.

DETAILED DESCRIPTION OF THE INVENTION

In one of its aspects, the invention comprises new compounds of the formula

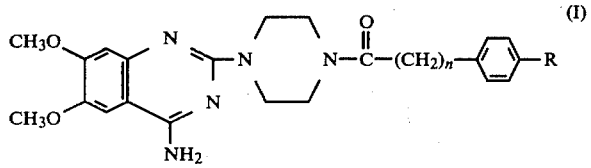

wherein n is 3, 4 or 5, and R is —NH$_2$, or —N$_3$, or a pharmaceutically acceptable salt thereof.

In another one of its aspects, the invention comprises new compounds of the formula

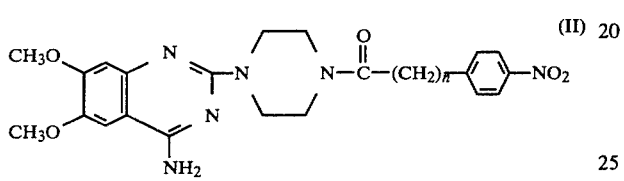

wherein n is 3, 4 or 5, which are useful as intermediates in the production of compounds of formula I.

In yet another one of its aspects, the invention resides in a method of producing α$_1$-antagonistic activity comprising contacting an α$_1$-adrenergic receptor with an amount of a compound of formula I effective to produce such activity.

In still yet another of its aspects, the invention resides in a method of producing α$_1$-antagonistic activity comprising administering to an animal requiring said treatment an amount of a compound of formula I effective to produce said activity.

In still yet another of its aspects, the invention resides in a method of treating hypertension comprising administering to an animal requiring said treatment an antihypertensive amount of a compound of formula I.

It has been determined that presently particularly preferred compounds of formula I, i.e., 4-amino-6,7-dimethoxy-2-[4-(5-[4-aminophenyl]pentanoyl)-piperazin-1-yl] quinazoline hydrochloride, and its 4-azidophenyl analog, exhibit a high degree of selectivity for α$_1$-adrenergic receptor sites and produce α$_1$-antagonism. The compounds are therefore useful in producing α$_1$-antagonistic activity. The compounds of formula I, and in particular 4-amino-6,7-dimethoxy-2-[4-(5-[4-aminophenyl]pentanoyl)piperazin-1-yl] quinazoline, may be employed in vivo to produce α$_1$-antagonistic activity, and are therefore useful in the treatment of hypertension. The compounds of formula I may also be used to produce α$_1$-antagonistic activity in vitro, and are therefore useful in the evaluation of α$_1$-agonistic and antagonistic characteristics of other compounds and in the isolation and/or characterization of α$_1$-adrenergic receptor sites.

Pharmaceutically acceptable acid addition salts of the compounds of formula I may be formed with organic or inorganic acids by methods well known in the art. For example, the base may be treated with an organic or inorganic acid in an aqueous miscible solvent, such as acetone or ethanol, with isolation of the salt by concentration or cooling, or in an aqueous immiscible solvent, such as ethyl ether or chloroform, or the like. Illustrative salts within the scope of the invention include maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, malate, mandelate, cinnamate citraconate, aspartate, stearate, palmitate, itaconate, glyucolate, p-aminobenzoate, glutamate, theophylline acetates, hydrochloride, hydrobromide sulfate, cyclohexylsulfamate, phosphate, nitrate, and the like salts.

The compounds of formula I may be prepared according to the following procedure:

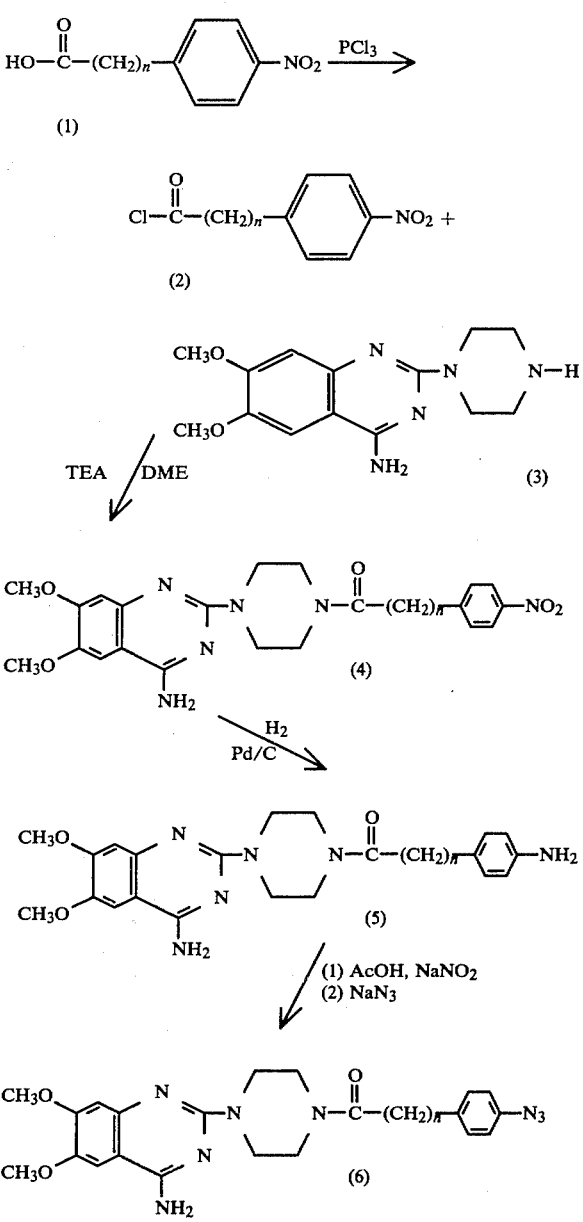

In accordance with the foregoing reaction scheme, a 4-nitrophenylalkanoic acid (1) is reacted with phosphorous trichloride, such as by heating at reflux in a suitable solvent, to obtain the corresponding acid chloride (2). The latter is reacted with 4-amino-6,7-dimethoxy-2-(1-piperazinyl) quinazoline (3) and triethyl amine (TEA) in dimethoxy ethane (DME) to obtain the 4-amino-6,7- dimethoxy-2-[4-[4-nitrophenyl]-alkanoyl)-1-piperazinyl] quinazoline intermediate (4). The 4-nitrophenyl intermediate (4) is then subjected to catalytic hydrogenation, such as in the presence of a palladium-on-carbon (Pd/C) catalyst, to obtain the desired 4-aminophenyl product (5).

The 4-aminophenyl product (5) may optionally be converted to the corresponding 4-azidophenyl compound (6), such as by reaction with acetic acid (AcOH) and sodium nitrite followed by sodium azide, and may additionally be tagged with a suitable marker label, such as $^{125}$I, optionally followed by azide formation as described above.

The foregoing may be better understood in connection with the following examples, which illustrate certain presently preferred embodiments of the invention.

EXAMPLE I

4-Amino-6,7-dimethoxy-2-[4-(5-[4-nitrophenyl]-pentanoyl)-1-piperazinyl] quinazoline hydrochloride 7.2 g. of 5(4-nitrophenyl) pentanoic acid, 7.2 g. of phosphorus trichloride and 86 ml. of benzene were mixed and heated at reflux for 1 hour. A small amount of yellow insoluble material was removed by filtration and the filtrate was concentrated under vacuum. The concentrated filtrate was then dissolved in 24 ml. of dimethoxyethane and added to a suspension of 12 g. of triethylamine and 6.0 g. of 4-amino-6,7-dimethoxy-2-(1-piperazinyl) quinazoline free base in 18 ml. of dimethoxyethane. The mixture was stirred at room temperature for 1 hour and then heated over a steam bath for 2 minutes. After cooling, the resulting solid was separated by filtration and separately washed with an aqueous solution of potassium hydroxide, with water and then with cold methanol, to obtain a solid having a melting point of 215°–216° C. The latter was converted to the hydrochloride salt in methanolic hydrochloric acid to obtain 7.2 g. of 4-amino-6,7-dimethoxy-2[4-(5-[4-nitrophenyl]pentanoyl)-1-piperazinyl] quinazoline hydrochloride having a melting point of 262°–265° C.

Analysis for hydrochloride ½H$_2$O: Calculated: C=55.55, H=5.97, N=15.56. Found: C=55.65, H=6.01, N=15.56.

EXAMPLE II

4-Amino-6,7-dimethoxy-2[4-(5-[4-aminophenyl]-pentanoyl]-1-piperazinyl] quinazoline dihydrochloride 5.19 g. of the product of Example I was hydrogenated in 250 ml. of 95% ethanol and 0.82 ml. of concentrated hydrochloric acid over 0.5 g. of 5% palladium-on-carbon catalyst under 3 atmospheres of hydrogen gas. After hydrogen uptake ceased, the catalyst was removed by filtration, and the filtrate was concentrated under vacuum to yield a solid. The solid was recrystallized from ethanol and 2-propanol to yield 4.25 g. of 4-amino-6,7-dimethoxy-2-[4-(5-[4-aminophenyl]pentanoyl)-1-piperazinyl] quinazoline dihydrochloride having a melting point of 244°–248° C.

Analysis for dihydrochloride ½H$_2$O: Calculated: C=54.95, H=6.46, N=15.38, Cl=12.97. Found: C=55.05, H=6.53, N=15.30, Cl=12.65.

EXAMPLE III

4-Amino-6,7-dimethoxy-2-[4-([4-aminophenyl]-alkanoyl)-1-piperazinyl] quinazoline hydrochlorides The procedure of Examples I and II is repeated using 4-(4-nitrophenyl) butyric acid and 6-(4-nitrophenyl) hexanoic acid as starting materials in place of 5-(4-nitrophenyl) pentanoic acid to obtain 4-amino-6,7-dimethoxy-2-[4-(4-[4-aminophenyl]butyryl)-1-piperazinyl] quinazoline hydrochloride and 4-amino-6,7-dimethoxy-2-[4-(6-[4-aminophenyl]hexanoyl)-1-piperazinyl] quinazoline hydrochloride, respectively.

EXAMPLE IV

4-Amino-6,7-dimethoxy-2-[4-([4-azidophenyl]-alkanoyl)-1-piperazinyl] quinazoline hydrochlorides The 4-aminophenyl products of Examples II and III are reacted in acetic acid with sodium nitrite and then sodium azide, followed by neutralization with concentrated ammonium hydroxide to obtain, respectively, 4-amino-6,7-dimethoxy-2-[4-(5-[4-azidophenyl]pentanoyl)-1-piperazinyl] quinazoline, 4-amino-6,7-dimethoxy-2-[4-(4-[4-azidophenyl]butyryl)-1-piperazinyl] quinazoline and 4-amino-6,7-dimethoxy-2-[4-(6-[4-azidophenyl]hexanoyl)-1-piperazinyl] quinazoline.

EXAMPLE V

The α-adrenergic receptor antagonistic activity of the compound of Example II is demonstrated in the isolated rabbit aorta as follows. Female rabbits, weighing 2 to 5 kg., are sacrificed by cervical dislocation. The thoracic cavity is immediately opened and the descending aorta is removed and placed in a petrie dish containing an aqueous buffer solution (Krebs buffer) of 119 mM NaCl, 25 mM NaHCO$_3$, 4.7 mM KCl, 1.5 mM MgSO$_4$, 1.2 mM KH$_2$PO$_4$, 2.5 mM CaCl$_2$, 11 mM glucose, 0.03 mM EDTA and 0.005 mM sodium ascorbate, adjusted to a pH of 7.4. The buffer solution is continuously aerated with a mixture of 95% O$_2$ and 5% CO$_2$ gases. The aorta is placed on cylindrical sticks and cleaned of excess fat and connective tissue, then cut into 2 tissue segments approximately 20 mm in length. Each segment of aorta is then spiraled in strips 3.5 mm wide by turning the stick as a scapel is applied, while leaving a section of 2-3 mm at each end of the aorta section intact. The spiraled tissue is mounted in an aerated (as above) tissue bath of 10 ml. of Kreb's buffer and is attached to a Grass force transducer with an initial applied tension of 2 grams. The tissue is allowed to equilibrate in the tissue bath at a temperature of 37±0.5° C. until the tension on the force transducer stabilizes at 2 grams. A cumulative dose-response curve of contraction for the tissue is determined by contacting the tissue with 10 to 400 ul of the standard agonist norepinephrine in log doses of from 1×10$^{-8}$ to 1×10$^{-3}$ M.

Upon contacting the tissue with the compound of Example II, the increase in contractile force produced by norepinephrine administration is inhibited, thereby demonstrating the α-adrenergic antagonistic activity of the compound. The degree of antagonistic activity is determined by varying the concentration of the test compound and measuring its pA$_2$ value, i.e., the negative log of the concentration of the test compound required to inhibit the norepinephrine response to the extent that the norepinephrine concentration must be doubled to obtain the maximum standard norepinephrine contractile response of the tissue. When measured in accordance with the foregoing procedure, the pA$_2$ values of the compound of Example II, prazosin and 2-(4-[4-aminobenzoyl]piperazin-1-yl)-4-amino-6,7-dimethoxyquinazoline (the 4-aminobenzoyl compound corresponding to the 4-azidobenzoyl compound of *Federation Proceedings* Vol. 41, No. 5, p. 1478, Mar. 10, 1982)

hereinafter referred to as "C"), were determined as set forth in Table I.

TABLE I

| Compound | pA$_2$ |
|---|---|
| Example II | 7.51 |
| prazosin | 8.58 |
| C | 7.45 |

EXAMPLE VI

The relative selectivity of the compounds of Example V for $\alpha_1$- or $\alpha_2$-adrenergic receptor sites is determined from radioligand binding data obtained in rat brain cortex tissue. The dissociation constant ($K_D$) is determined for the radioligand ($^3$H) prazosin with respect to $\alpha_1$-adrenergic receptors and for the radioligand [$^3$H] yohimbine with respect to $\alpha_2$-adrenergic receptors according to the method of Hoffman et al., *Life Sciences*, Vol. 28, pp 265-272. The concentration of the test compound (IC$_{50}$) required to displace 50% of the total specific binding of the radioligand is determined and used to calculate the nanamolar dissociation constant (KI) of the test compound for a particular $\alpha$-adrenergic receptor according to the following relationship:

$$KI = \frac{IC_{50}}{1 + \frac{[L]}{K_D}}$$

where [L] is the radiologand concentration and $K_D$ is the dissociation constant for the radioligand. The KI value provides quantitative measure of the affinity of a test compound for a receptor site, with relatively lower KI values indicating relatively higher affinities. The KI values obtained for the compounds of Example V are as set forth in the following Table II:

TABLE II

| Compound | KI (nM) a$_1$ | KI (nM) a$_2$ | KI$\alpha_2$ / KI$\alpha_1$ |
|---|---|---|---|
| Example II | 4.5 | 4,925.3 | 1,094.5 |
| prazosin | 1.3 | 526.6 | 405.1 |
| C | 17.0 | 12,426.0 | 730.9 |

EXAMPLE VII

The therapeutic activity of the compound produced by Example II is demonstrated in vivo by its ability to decrease arterial blood pressure and/or heart rate in the spontaneously hypertensive rat as follows: Two groups of Okamoto rats, which develop hypertension spontaneously when reaching young adulthood, are deprived of food for a period of 16 hours and are placed in semi-restraining wire mesh cylinders maintained at a constant temperature of 36° C. An occluding cuff, operatively connected to a programmed sphygmomanometer, is placed over the tail of each rat of the group and retained near the tail base. The pressure of each cuff is automatically cyclically increased within the range of from 0 to 250 mm Hg. at the rate of 10 mm Hg./sec., the total inflation and deflation time of each cycle being 50 seconds, with a 10 second rest period between cycles. A photocell is placed distal to the cuff to detect pulses resulting from the forward motion of blood flow with each heartbeat of the rat. As the pressure in the cuff increases, measurable pulses disappear at the point where the cuff pressure equals the arterial blood pressure. Measurable pulses reappear during deflation at approximately the same pressure, and arterial blood pressure is thereby established by cuff pressure at the point of pulse appearance. The heart rate is determined from the arterial pulse wave. Doses of 30 or 100 mg./kg. of the preferred compound of Example II are administered orally to each rat of the test groups and five interference-free signals are recorded on a Model 7 Grass polygraph for each rat at various measurement periods following administration. By following the foregoing procedure, the preferred compound of Example II is shown to decrease the arterial blood pressure of rats of each group.

The compounds of the invention can be administered in any effective pharmaceutically acceptable form to warm blooded animals, e.g., in oral, parenteral or infusable dosage forms, or as a buccal or nasay spray. Suitable parenteral routes of administration include, for example, intramuscular, intravenous, intraperitoneal or subcutaneous administration of the compounds.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents in to the compositions. They can also be manufactured in the form of sterile solid compositions which can be dissolved in sterile water, or other sterile injectable medium, immediately before use.

Solid dosage forms for oral administration include capsules, tablets, pills, powders, and granules. In such solid dosage forms, the active compund may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions may also comprise adjuvants, such as wetting agents, emulsifying and suspending agents, and sweetening, flavoring and perfuming agents.

Actual dosage levels of active ingredient in the compositions of the invention may be varied so as to obtain an amount of active ingredient effective to obtain a desired therapeutic response for a particular composition and method of administration. The selected dosage level therefore depends upon the desired therapeutic effect, on the route of administration, on the desired duration of treatment and other factors. Generally, it is contemplated that dosage levels of about 1 to about 2000, more preferably about 5 to about 500 and most preferably about 10 to about 200 mg. of active ingredient per kg. of body weight per day administered orally will be effective in the treatment of a mammalian patient suffering from hypertension. If desired, the daily dose may be divided into multiple doses for administration, e.g., two to four separate doses per day.

As is apparent from the foregoing, the compounds of the invention are also useful in the production of $\alpha_1$-adrenergic antagonistic activity in vitro. The highly selective nature of the compounds for $\alpha_1$-adrenergic receptors makes them particularly useful in the isolation and characterization of $\alpha_1$-adrenergic receptors, in the evaluation of $\alpha_1$-adrenergic activity of other compounds, as diagnostic reagents and the like. The azido compounds of the invention may additionally be irreversibly incorporated into $\alpha_1$-adrenergic receptor sites by photolysis as described in connection with the compound (2-[4-(4-azido-benzoyl-piperazin-1-yl]-4-amino-6,7-dimethoxy quinazoline in Hess et al., "Photoaffinity Label of the $\alpha_1$-Adrenergic Receptor," *Federation Proceedings*, Vol. 41, No. 5, at #7064, p. 1478.

Accordingly, in some uses, it may be desirable to immobilize the compounds of the invention, such as on a suitable solid support, to facilitate isolation of $\alpha_1$-adrenergic receptors from a homogenized membrane or tissue suspension, or for other purposes. As used herein, the term "solid support" refers to insoluble materials sorptive for the compounds or to which the compounds may be fixed either by direct bonding or through an indirect linking agent. Suitable materials of this type include hydrocarbon polymers such as polystyrene, polypropylene, polybutylene, butyl rubber and other synthetic rubbers. Other suitable organic polymers include silastic rubber, polyesters, polyamides, cellulose and cellulosic derivatives, acrylates, methacrylates, and vinyl rubber polymers such as vinyl chloride, polyvinyl chloride, copolymers and graft copolymers of the foregoing polymeric materials. In addition, the solid support surface may comprise silica gel, silicone wafers, and glass insoluble protein metals. The solid support surface may be in the form of microparticles, beads, tubes, strips, disks, microtitration plates and the like. A presently particularly preferred solid support surface is agarose, whose use in the purification of $\alpha_1$-adrenergic receptors is described in Graham, et al., "Solubilization and Purification of the $\alpha_1$-Adrenergic Receptor Using a Novel Affinity Resin," *Proc. Natl. Acad. Sci.*, Vol. 79, pp. 2186–2190.

In addition to the foregoing, the use of the compound of the invention for diagnostic and/or analytical purposes may in some cases be facilitated by labeling the compounds with a suitable marker moiety. The compounds of the invention may be directly or indirectly labeled with fluorescent dyes, enzymes or radioactive labels by conventional methods to enable their tracing and/or quantification. Suitable readioactive labels include, for example, $^3H$, $^{125}I$, and the like.

What is claimed is:

1. A compound of the formula

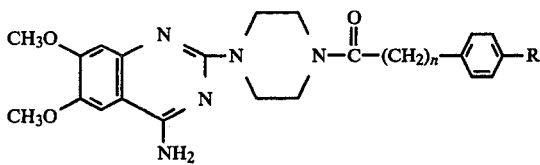

wherein n is 3, 4 or 5, and R is —NH$_2$ or —N$_3$, or a pharmaceutically acceptable acid addition salt thereof.

2. A compound of claim 1 wherein n is 4.

3. A compound of claim 2 wherein R is —NH$_2$.

4. The compound 4-amino-6,7-dimethoxy-2[4-(5-[4-aminophenyl]pentanoyl)-1-piperazinyl] quinazoline or a pharmaceutically acceptable acid addition salt thereof.

5. The compound of claim 4, 4-amino-6,7-dimethoxy-2[4-(5-[4-aminophenyl]pentanoyl)-1-piperazinyl] quinazoline dihydrochloride.

6. The compound 4-amino-6,7-dimethoxy-2[4-(5-[4-azidophenyl]pentanoyl)-1-piperazinyl] quinazoline or a pharmaceutically acceptable acid addition salt thereof.

7. An intermediate compound of the formula

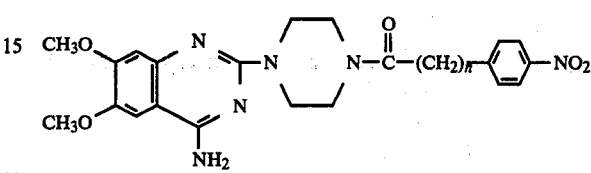

wherein n is 3, 4 or 5.

8. The compound of claim 7 wherein n is 4.

9. An antihypertensive composition comprising a therapeutically effective amount of a compound of the formula

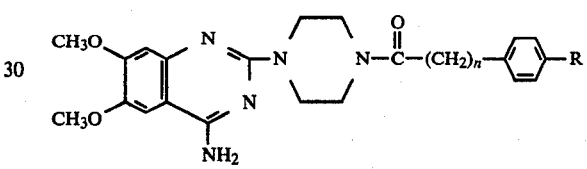

wherein n is 3, 4 or 5, and R is —NH$_2$ or —N$_3$, or a pharmaceutically acceptable acid addition salt thereof, together with a pharmaceutically acceptable carrier or diluent.

10. A pharmaceutical composition of claim 9 comprising 4-amino-6,7-dimethoxy-2-[4-(5-[4-aminophenyl]-pentanoyl-1-piperazinyl] quinazoline or a pharmaceutically acceptable acid addition salt thereof, together with a pharmaceutically acceptable carrier or diluent.

11. A pharmaceutical composition of claim 9 comprising 4-amino-6,7-dimethoxy-2[4-(5-[4-azidophenyl]-pentanoyl)-1-piperazinyl] quinazoline or a pharmaceutically acceptable acid addition salt thereof, together with a pharmaceutically acceptable carrier or diluent.

12. A method of producing $\alpha_1$-antagonistic activity which comprises administering to an animal an amount of a compound of the formula

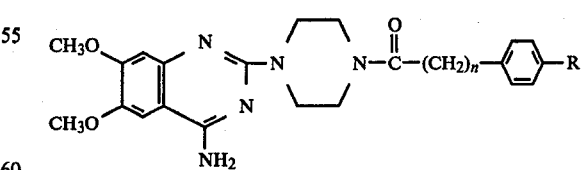

wherein n is 3, 4 or 5, and R is —NH$_2$ or —N$_3$, or a pharmaceutically acceptable acid addition salt thereof, sufficient to produce said activity.

13. The method of claim 12 wherein said compound is 4-amino-6,7-dimethoxy-2[4-(5-[4-aminophenyl]pentanoyl)-1-piperazinyl] quinazoline, or a pharmaceutically acceptable acid addition salt thereof.

14. A method of producing antagonistic activity in an $\alpha_1$-adrenergic receptor comprising administering to a patient in need of such treatment a therapeutically effective amount of a compound of the formula

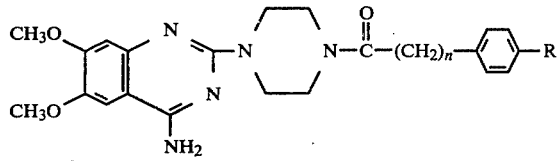

wherein n is 3, 4 or 5, and R is —NH$_2$ or —N$_3$, or a pharmaceutically acceptable acid addition salt thereof, sufficient to produce said activity.

15. The method of claim 14 wherein said compound is 4-amino-6,7-dimethoxy-2[4-(5-[4-aminophenyl]pentanoyl)-1-piperazinyl] quinazoline or a pharmaceutically acceptable acid addition salt thereof.

16. The method of claim 14 wherein said compound is 4-amino-6,7-dimethoxy-2[4-(5-[4-azidophenyl]pentanoyl)-1-piperazinyl] quinazoline or a pharmaceutically acceptable acid addition salt thereof.

* * * * *